United States Patent
Yang

(10) Patent No.: US 10,842,904 B2
(45) Date of Patent: Nov. 24, 2020

(54) STERILIZATION AND DRYING DEVICE

(71) Applicant: Jung Hee Yang, Gimpo-si (KR)

(72) Inventor: Jung Hee Yang, Gimpo-si (KR)

( * ) Notice: Subject to any disclaimer, the term of this patent is extended or adjusted under 35 U.S.C. 154(b) by 249 days.

(21) Appl. No.: 15/902,072

(22) Filed: Feb. 22, 2018

(65) Prior Publication Data

US 2019/0060504 A1 Feb. 28, 2019

(30) Foreign Application Priority Data

Aug. 22, 2017 (KR) .................. 10-2017-0105999

(51) Int. Cl.
| | | |
|---|---|---|
| *A61L 9/18* | (2006.01) | |
| *A61L 2/04* | (2006.01) | |
| *A61L 2/08* | (2006.01) | |
| *F26B 3/06* | (2006.01) | |
| *F26B 21/00* | (2006.01) | |
| *A47L 23/20* | (2006.01) | |
| *F26B 9/00* | (2006.01) | |

(52) U.S. Cl.
CPC ............ *A61L 9/18* (2013.01); *A47L 23/205* (2013.01); *A61L 2/04* (2013.01); *A61L 2/085* (2013.01); *F26B 3/06* (2013.01); *F26B 9/003* (2013.01); *F26B 21/001* (2013.01); *F26B 21/006* (2013.01); *A61L 2202/26* (2013.01)

(58) Field of Classification Search
CPC ... A61L 9/18; A61L 2/04; A61L 2/085; A61L 2202/26
See application file for complete search history.

(56) References Cited

U.S. PATENT DOCUMENTS

| | | | | |
|---|---|---|---|---|
| 3,513,564 A | * | 5/1970 | Gramprie | F26B 21/006 34/104 |
| 2007/0044340 A1 | * | 3/2007 | Christian | A47L 23/205 34/104 |
| 2015/0004063 A1 | * | 1/2015 | Lee | A61L 9/16 422/121 |

FOREIGN PATENT DOCUMENTS

| | | |
|---|---|---|
| KR | 20-0439102 Y1 | 3/2008 |
| KR | 10-1188774 B1 | 10/2012 |
| KR | 10-2017-0069393 A | 6/2017 |

* cited by examiner

*Primary Examiner* — Kevin Joyner
(74) *Attorney, Agent, or Firm* — Korus Patent, LLC; Seong Il Jeong

(57) ABSTRACT

Disclosed herein is a sterilization and drying device. The sterilization and drying device includes: a body configured to be coupled to the inside of a sterilization target, and to suck and discharge internal air of the sterilization target; a silicon carbide honeycomb heater installed inside the body, and configured to sterilize, purify, dry, and heat the sucked air and discharge the sterilized, purified, dried, and heated air; an air circulation fan installed behind the silicon carbide honeycomb heater, and configured such that the internal air of the sterilization target is sucked, passed through the silicon carbide honeycomb heater, and then discharged; and a battery installed on one side of the air circulation fan, and configured to supply power to the silicon carbide honeycomb heater and the air circulation fan.

8 Claims, 6 Drawing Sheets

STERILIZATION AND DRYING DEVICE

BACKGROUND

1. Technical Field

Various embodiments of the present invention relate to a sterilization and drying device.

2. Description of the Related Art

For example, a washed sterilization target is naturally dried in such a manner as to put the sterilization target in an inclined manner in the sun or shade or to hang it on a drying rack.

However, such a drying method takes an excessively long drying time, and cannot dry a sterilization target in the rainy and winter seasons due to moisture and low temperature. Rather, a problem occurs in that mold is generated inside the sterilization target.

Furthermore, leather sterilization targets, such as shoes or boots, cannot be washed using water, and thus inconvenience arises in that the insides of the sterilization targets must be frequently dried. Moreover, when such a sterilization target is left in the state where the moisture inside the sterilization target has not been eliminated, the hygienic state of the sterilization target becomes significantly poor in that bacteria, such as fungi, grow and serious malodor occurs.

Conventionally, in order to mitigate the above problems, sterilization target driers including an ultraviolet (UV) lamp, a positive temperature coefficient (PTC) metal heater, or the like have been used.

However, the UV lamp has a critical problem in that it generates ultraviolet rays harmful to the human body, whereas the PTC metal heater also has a critical problem in that it generates electromagnetic waves harmful to the human body. Moreover, the conventional sterilization target dryers have problems in that a long drying time is taken because drying air is not efficiently provided inside a sterilization target, and in that an unnecessarily large amount of drying air is supplied to the outside of a sterilization target in order to dry the inside of the sterilization target, and thus deformation may occur due to expansion and contraction. As a result, a problem arises in that the life span of the sterilization target is reduced.

The above-described information disclosed in the description of the related art is intended merely to improve understanding of the related art of the present invention, and may include information that does not constitute the conventional art.

SUMMARY

An object of the present invention is to provide a sterilization and drying device which does not generate ultraviolet rays and/or electromagnetic waves and which can sterilize, purify, dry and heat air inside a sterilization target by means of far-infrared rays.

According to an aspect of the present invention, there is provided a sterilization and drying device, including: a body configured to be coupled to the inside of a sterilization target, and to suck and discharge internal air of the sterilization target; a silicon carbide honeycomb heater installed inside the body, and configured to sterilize, purify, dry, and heat the sucked air and discharge the sterilized, purified, dried, and heated air; an air circulation fan installed behind the silicon carbide honeycomb heater, and configured such that the internal air of the sterilization target is sucked, passed through the silicon carbide honeycomb heater, and then discharged; and a battery installed on one side of the air circulation fan, and configured to supply power to the silicon carbide honeycomb heater and the air circulation fan.

The body may have a cylindrical shape which is empty in a lengthwise direction, and may include a plurality of air inlets which is formed on the inside surface of the body in a lengthwise direction and which extends from the front of the body to the back of the air circulation fan.

The air inlets may further include a plurality of air suction holes which is formed through the body.

The internal air of the sterilization target may be sucked to the air circulation fan through the air suction holes of the air inlets, and the air sterilized, purified, dried, and heated via the silicon carbide honeycomb heater may be discharged through the front of the body.

The sterilization and drying device may further include a front cover which is coupled to the front of the body and which includes a plurality of air suction holes configured to suck the internal air of the sterilization target and an air outlet configured to discharge the sterilized, purified, dried, and heated air.

The body may include: an inner body coupled to the air outlet of the front cover; an outer body coupled to the outer circumference of the front cover; and a plurality of air inlets configured to suck air from the air suction holes of the front cover between the inner body and the outer body, and to transfer the air to the air circulation fan.

The front cover may further include coupling protrusions extended backward; the body may further include coupling depressions formed between the inner body and the outer body; and the coupling protrusions of the front cover may be coupled to the coupling depressions of the body.

The body may further include a retainer ring installed behind the inner body and the outer body and configured such that the silicon carbide honeycomb heater is coupled thereto.

The silicon carbide honeycomb heater may further include coupling rings configured to be coupled to the retainer ring, and the retainer ring and the coupling rings may be made of thermal insulators configured to prevent heat from being transferred from the honeycomb heater to the body.

According to another aspect of the present invention, there is provided a sterilization and drying device, including: a front cover configured such that a plurality of air suction holes is formed to suck internal air of a sterilization target and such that an outlet is formed to discharge sterilized and dried air; a body coupled to the front cover, and configured such that air inlets formed in regions corresponding to the air suction holes and an air outlet formed in a region corresponding to the air outlet are included; a silicon carbide honeycomb heater coupled to the back of the body, and configured to have a size corresponding to that of the air outlet; and a back cover coupled to the silicon carbide honeycomb heater, and configured to block the back of the body.

The sterilization target may be one of a shoe, a garment, a shoe closet, and a pet dog.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1A:
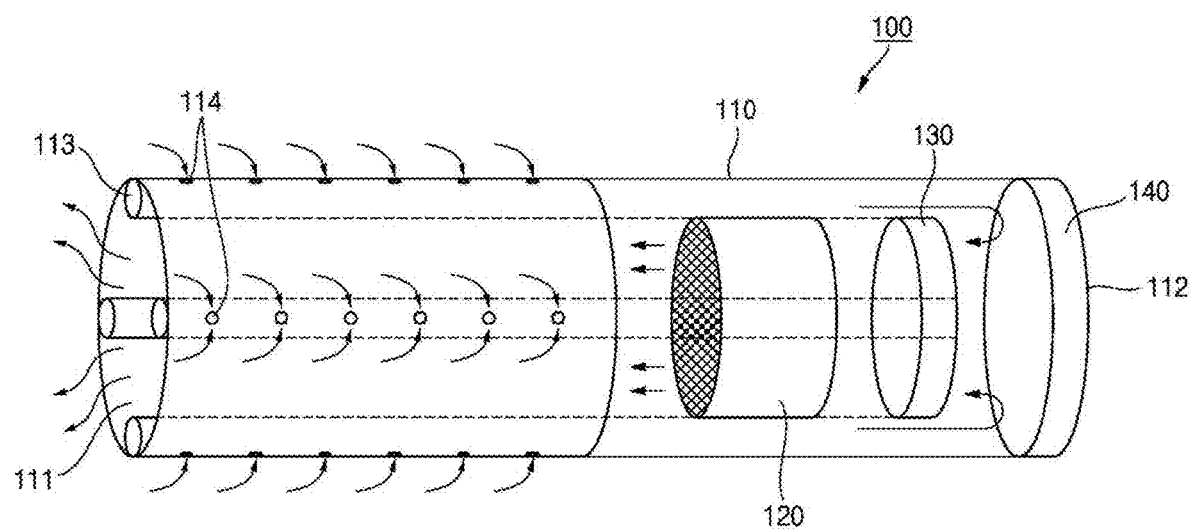
FIGS. 1a to 1c are a schematic diagram, perspective view and front view of a sterilization and drying device according to various embodiments of the present invention, respectively.

Embodiments of the present invention will be described in detail below with reference to the accompanying drawings.

The embodiments of the present invention are provided to more fully describe the present invention to those skilled in the art. The embodiments may be modified in various different forms, and the scope of the present invention is not limited to the following embodiments. Rather, these embodiments are provided to make the present disclosure more reliable and complete and to convey the spirit of the present invention to those skilled in the art.

Furthermore, in the following drawings, the thickness or size of each layer may be exaggerated for the sake of easy description and clarity, and the same reference symbols denote the same component throughout the drawings. As used in the present specification, the term "and/or" refers to the inclusion of all combinations of one or more of listed items. Furthermore, in the present specification, the term "connected" refers to not only a case where member A is directly connected to member B but also a case where member A is indirectly connected to member B with member C interposed therebetween.

The terms used therein are each intended to describe a specific embodiment, but is not intended to limit the present invention. As used in the present specification, a singular expression may include a plural expression unless otherwise stated clearly in the context. Furthermore, when used in the present specification, the term "include," "comprise" and "have" are each intended to specify shapes, numbers, steps, operations, components, and/or a combination thereof, but are not intended to exclude the presence or addition of another shape, another number, another step, another operation, another component, another component, and/or another combination.

In the present specification, although the terms first, second, third, etc. may be used herein to describe various members, components, regions, layers and/or sections, these members, components, regions, layers and/or sections should not be limited by these terms. These terms are only used to distinguish one member, component, region, layer, or section from another member, component, region, layer, or section. Accordingly, a first member, component, region, layer, or section discussed below could be termed a second member, component, region, layer, or section without departing from the teachings of the present invention.

Spatially relative terms, such as "beneath," "below," "lower," "above" and the like, may be used herein for ease of description to describe the relationship between one element or feature and another element or feature as illustrated in the figures. It will be understood that the spatially relative terms are intended to encompass different orientations of the element or feature in use or operation, in addition to the orientation depicted in the figures. For example, if an element or feature in the figures is turned over, the element described as being placed "below" another element or feature may be then placed "above" the other element or feature. Accordingly, the exemplary term "below" can encompass both orientations of above and below.

Furthermore, the sterilization target described herein may be, for example, but not exclusively, one of a shoe, a garment, a shoe closet, and a pet dog.

Figure 1B:
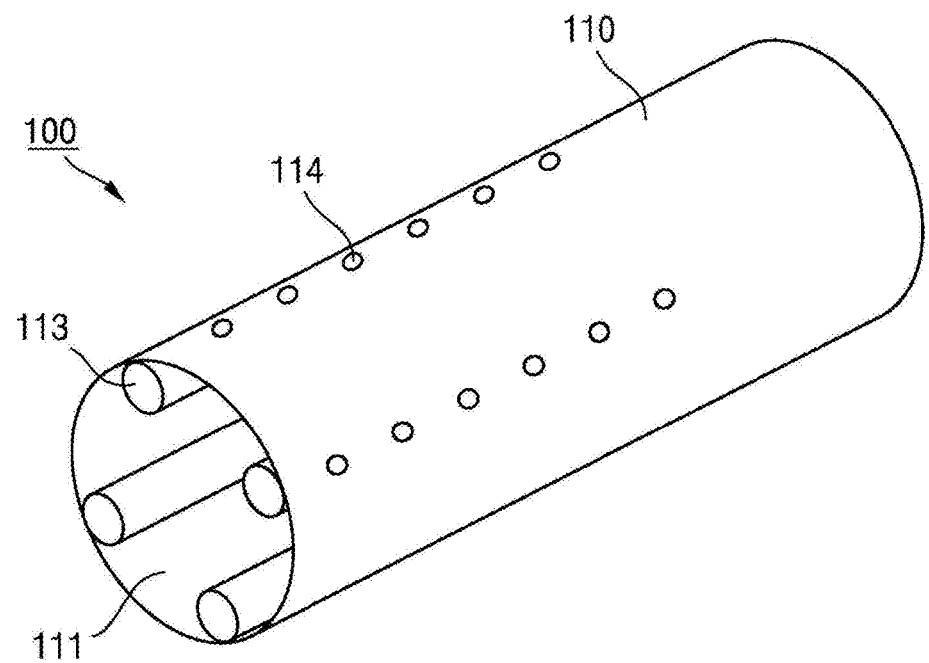
Figure 1C:
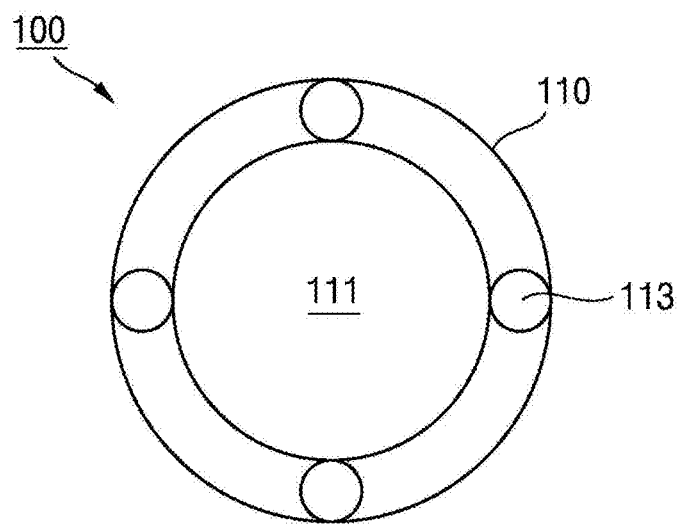

Referring to FIGS. 1a to 1c, a schematic view, perspective view and front view of a sterilization and drying device 100 according to various embodiments of the present invention are shown.

As shown in FIGS. 1a to 1c, the sterilization and drying device 100 according to the various embodiments of the present invention may include a body 110, a silicon carbide honeycomb heater 120 coupled inside the body 110, an air circulation fan 130 coupled inside the body 110, and a battery 140 coupled inside the body 110.

The body 110 is coupled inside a sterilization target, and functions to suck and discharge the internal air of the sterilization target. The body 110 has, for example, but not exclusively, an approximately cylindrical shape which is empty in a lengthwise direction. More specifically, the body 110 may include an air outlet 111 formed in the front of the body 110 and a back cover 112 formed in the back of the body 110.

Furthermore, the body 110 may include a plurality of air inlets 113 which is formed on the inside surface of the body 110 in a lengthwise direction and which extends from the front of the body 110 to a location behind the air circulation fan 130. Although four air inlets 113 are shown in the drawings, the present invention is not limited to four, and the number of air inlets 113 may be smaller or larger than four.

Furthermore, the air inlets 113 may include a plurality of air suction holes 114 which is formed to pass through the body 110. Accordingly, air inside the sterilization target is sucked and guided to the air circulation fan 130 through the air suction holes 114 of the air inlets 113, and air sterilized, purified, dried and heated via the silicon carbide honeycomb heater 120 is discharged through the air outlet 111 formed through the front of the body 110.

The body 110 is made of, for example, but not exclusively, thermoplastic resin such as polyethylene, polypropylene, polyvinyl chloride, polystyrene, ABS resin, AS resin, methacrylic resin, polyvinyl alcohol, polyvinylidene chloride or engineering plastic, thermosetting resin phenol resin such as urea resin, melamine resin, alkyd resin, unsaturated polyester resin, epoxy resin, polyurethane resin, silicon resin or diallylphtalate resin, or the like which has superior thermal resistance and chemical resistance. Furthermore, the body 110 may be made of ceramic, metal, or the like.

The silicon carbide honeycomb heater 120 is installed inside the body 110, and functions to sterilize, purify, dry and heat air sucked through the air inlets 113 of the above-described body 110, to pass the air therethrough, and to discharge the air through the air outlet 111 formed through the front of the body 110. The silicon carbide honeycomb heater 120 may have, for example, but not exclusively, an approximately column shape having a predetermined thickness, and may include a plurality of honeycomb patterns which is formed in the silicon carbide honeycomb heater 120 and through which air passes.

The silicon carbide honeycomb heater 120 may include, for example, but not exclusively, at least one first composition selected from among silicon Si, carbon C and boron carbide and at least one second composition selected from among an austenitic heating alloy (an NiCr alloy), a ferritic heating alloy (an FeCrAl alloy), copper Cu, silicon Si and a silmin alloy (an Al—Si alloy), in silicon carbide SiC.

As an example, the first composition contains 5 parts by weight of at least one of silicon Si, carbon C, and boron carbide, in addition to 50-95 parts by weight of silicon carbide SiC. In this case, silicon carbide SiC is the principal material of the honeycomb heater 120. Silicon carbide SiC is heated and emits heat at high energy efficiency. In particular, Silicon carbide SiC does not emit electromagnetic waves.

Furthermore, as an example, the cell density of the honeycomb heater 120 may range from 20 to 200 CPSI (cell per square inch), the sectional size of the honeycomb heater 120 may range from about 20 to 50 mm, and the length of the honeycomb heater 120 may range from 20 to 50 mm.

Furthermore, the second composition may perform a resistance control function. As an example, among the second compositions, the austenitic heating alloy (an NiCr alloy) has a superior heat emission property, high creep strength, high radiation rate, and superior corrosion resistance. Furthermore, among the second compositions, the ferritic heating alloy (an FeCrAl alloy) has a long life span, a low density, high specific resistance, and superior resistance to sulfide corrosion. Furthermore, among the second compositions, the silmin alloy (an Al—Si alloy) is suitable for sand and mold casting and die casting.

In particular, an Al—Si-based alloy, i.e., one of the sand or mold casting alloys, is referred to as silmin. The Al—Si-based alloy can be easily casted. In particular, when the Al—Si-based alloy has a composition close to the eutectic point of an Al—Si-based alloy, hot brittleness is eliminated, and flowability, weldability and corrosion resistance become excellent. Accordingly, the Al—Si-based alloy is widely and chiefly used for thick large-sized and complex castings. Furthermore, an Al-high Si alloy, i.e., one of the die casting alloys, is an Al-12% Si binary alloy which has the same composition as an Al—Si-based alloy (AC3A). When the quantity of impurities, particularly Fe, is low during die casting, Al is deposited on a mold. Accordingly, generally, when about 1% of Fe is added, optimum castability and strength are achieved. An Al—Si-based alloy (ADC7), i.e., another die casting alloy, has superior elongation, superior pressure resistance, and superior corrosion resistance.

The parts by weight of the first composition may range from about 45 to about 55, and the parts by weight of the second composition may range from about 45 to about 55. When the parts by weight of the first composition are smaller than about 45, electric resistance decreases, and thus power consumption may increase. In contrast, when the parts by weight of the first composition are larger than about 55, electric resistance increases, and thus heat generation efficiency may decrease.

The air circulation fan 130 is installed behind the silicon carbide honeycomb heater 120 inside the body 110, and functions to suck the internal air of the sterilization target, to pass the air through the silicon carbide honeycomb heater 120, and to discharge the air. In other words, the air circulation fan 130 has a diameter similar to the inner diameter of the body 110, and is installed in an inside area formed by the plurality of air inlets 113. Accordingly, air inside the sterilization target is sucked from the air inlets 113 and the air suction holes 114, is passed through the silicon carbide honeycomb heater 120, and is then discharged.

The battery 140 is installed on, for example, but not exclusively, one side of the air circulation fan 130, and functions to supply power to the silicon carbide honeycomb heater 120 and the air circulation fan 130. In particular, the battery 140 is installed behind the air circulation fan 130, and is prevented from being heated by the silicon carbide honeycomb heater 120 in such a manner that the battery 140 is cooled by the air sucked by the air circulation fan 130. The battery 140 may include, for example, but not exclusively, a lithium-ion battery, a lithium-polymer battery, a lithium-ion polymer battery, and an all-solid-state battery which are rechargeable. In particular, when an all-solid-state battery is used as the battery 140, liquid is not present inside the battery, and thus the battery 140 has no risk of being expanded or exploded regardless of heat transferred from the silicon carbide honeycomb heater 120.

Meanwhile, the battery 140 supplies a power ranging from about 3.2 to 320 V (in the case where a boosting circuit is adopted) to the silicon carbide honeycomb heater 120, thereby enabling the heating temperature of the silicon carbide honeycomb heater 120 to reach 1 to 25° C./sec.

As described above, the sterilization and drying device 100 according to the various embodiments of the present invention sucks air inside a sterilization target via the air suction holes 114 of the body 110, the air inlets 113 and the air circulation fan 130, sterilizes, purifies, dries and heats the air via the silicon carbide honeycomb heater 120, and discharges the air into the sterilization target via the air outlet 111 of the body 110, thereby rapidly heating and drying the sterilization target and also sterilizing and purifying the inside of the sterilization target.

Figure 4:
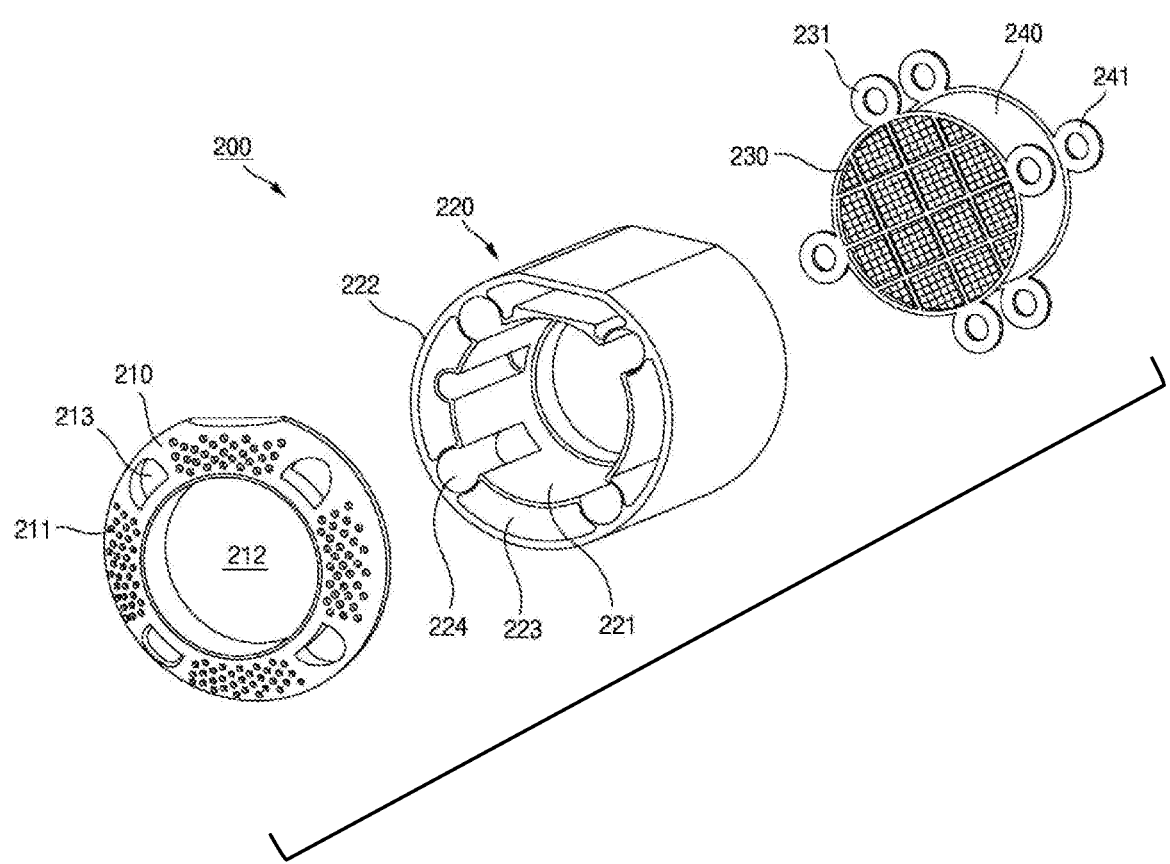
FIG. 4 is an exploded perspective view of a sterilization and drying device according to various embodiments of the present invention.

Meanwhile, the principal components/materials of the sterilization and drying device 100 shown in FIGS. 1a to 1c may be applied to the sterilization and drying device 200 shown in FIG. 4 in the same manner.

Figure 2:
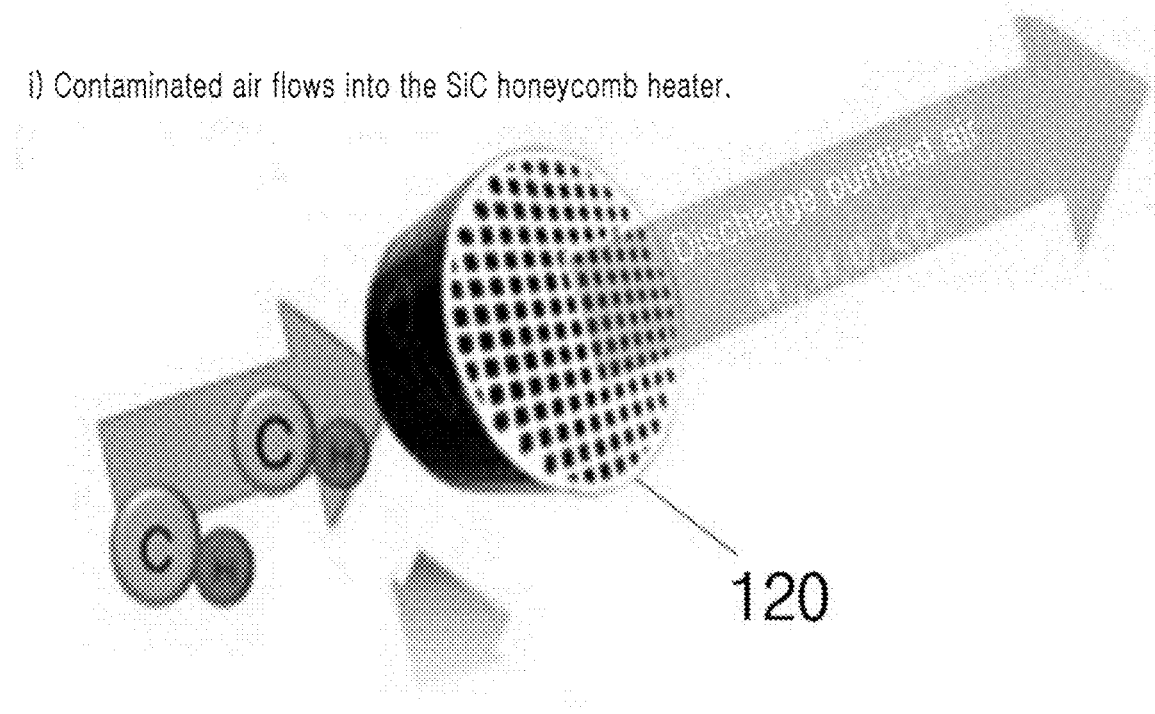
FIG. 2 is a schematic diagram showing an example in which hot wind and far-infrared rays are generated by a silicon carbide honeycomb heater in the sterilization and drying device according to the various embodiments of the present invention.

Referring to FIG. 2, an example in which hot wind and far-infrared rays are generated by a silicon carbide honeycomb heater 120 in the sterilization and drying device 100 according to the various embodiments of the present invention is schematically shown.

As shown in FIG. 2, cold air on one side is dried and heated via the silicon carbide honeycomb heater 120 and supplied to an object to be heated in the form of hot wind, and far-infrared rays are radiated from the silicon carbide honeycomb heater 120 onto the object to be heated, thereby sterilizing and purifying the object to be heated.

Figure 3A:
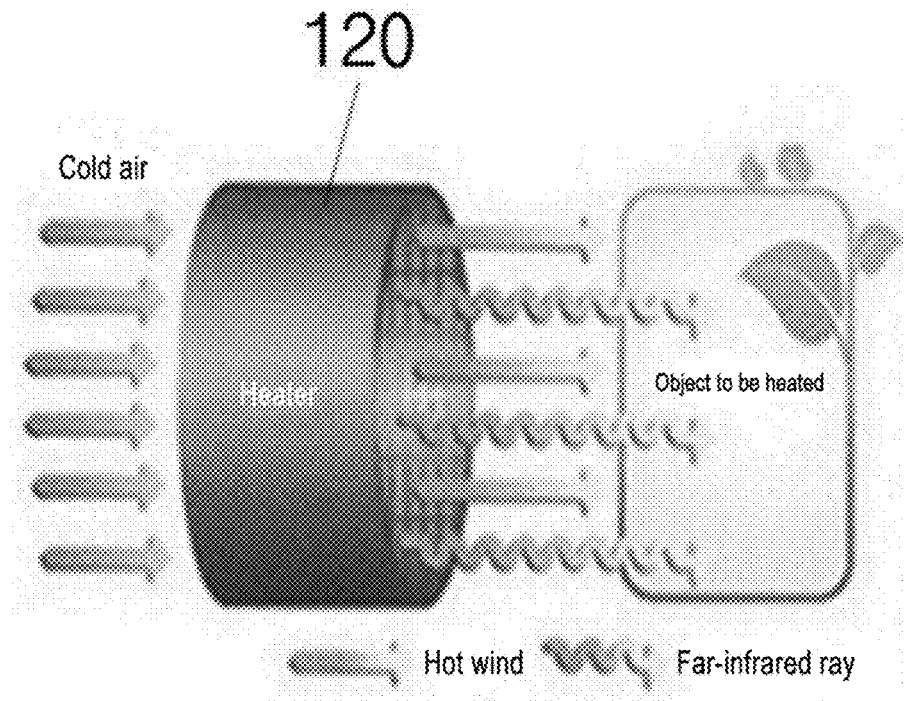
FIGS. 3a to 3c are schematic diagrams showing the sterilization principle of the sterilization and drying device according to the various embodiments of the present invention.
Figure 3B:
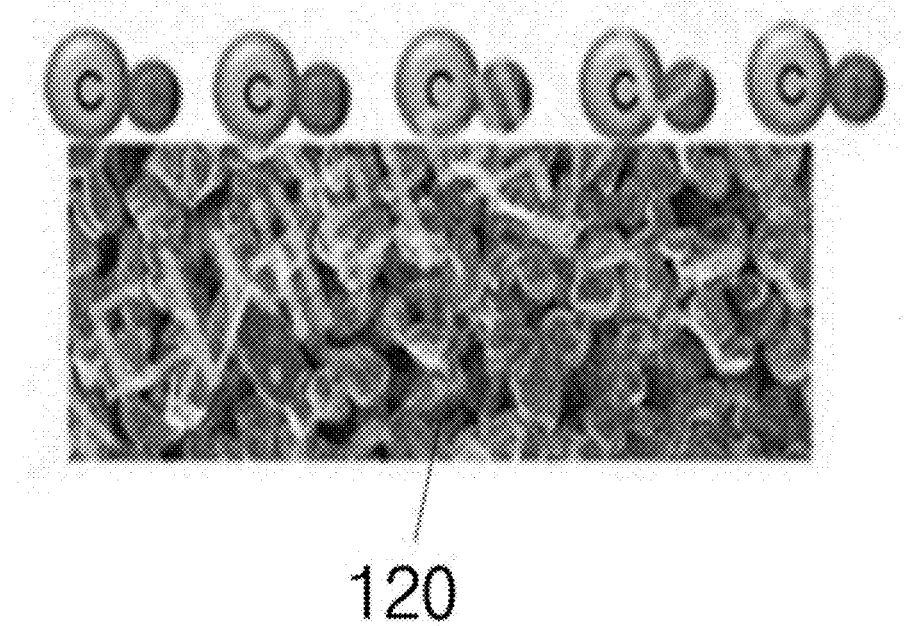
Figure 3C:
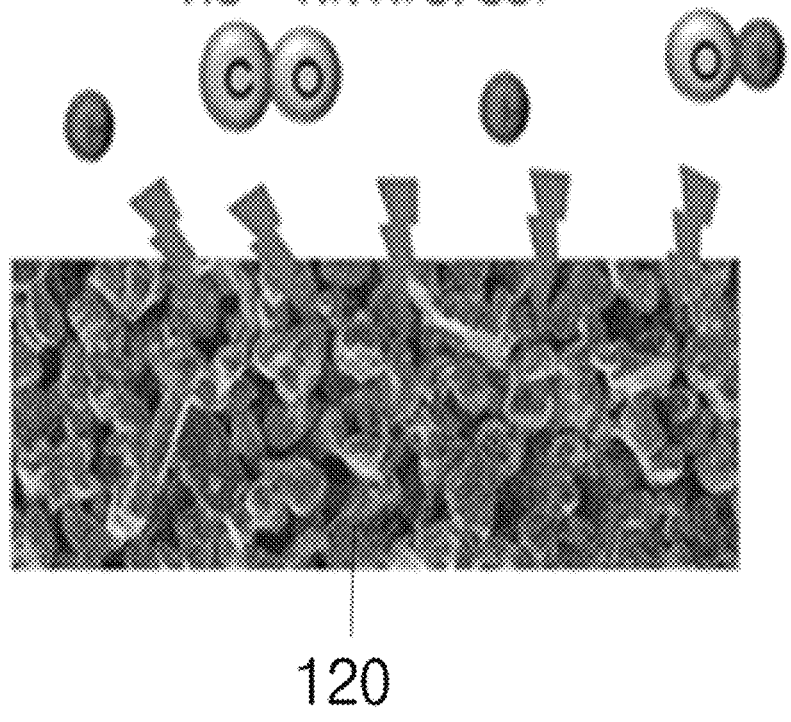

Referring to FIGS. 3a to 3c, the sterilization principle of the sterilization and drying device 100 according to the various embodiments of the present invention is schematically shown.

As shown in FIGS. 3a to 3c, when contaminated air is passed through the silicon carbide honeycomb heater 120, it is discharged as purified air. For example, as shown in FIG. 3b, when contaminated air including HC is adsorbed/attached onto the surface of the silicon carbide honeycomb heater 120, HC is decomposed into $H_2$, $H_2O$, and CO and sterilized/purified by far-infrared rays of the silicon carbide honeycomb heater 120, as shown in FIG. 3c.

Referring to FIG. 4, an exploded perspective view of a sterilization and drying device 200 according to various embodiments of the present invention is shown.

As shown in FIG. 4, the sterilization and drying device 200 according to the various embodiments of the present invention may include a front cover 210, a body 220, a silicon carbide honeycomb heater 230, and a back cover 240.

The front cover 210 is coupled to the front of the body 220 in an approximately circular ring shape. The front cover 210 may include a plurality of air suction holes 211 configured to suck air inside a sterilization target and an air outlet 212 configured to discharge sterilized, purified, dried, and heated air. In other words, the front cover 210 may include the plurality of air suction holes 211 formed through the inner circumference of the front of the front cover 210 and the relatively large air outlet 212 formed through the center of the front of the front cover 210. Furthermore, the front cover 210 may further include a plurality of coupling protrusions 213 which is formed through the inner circumference of the front of the front cover 210 and which is extended to a predetermined length.

Furthermore, the body 220 is formed in an approximately cylindrical shape, and may include an inner body 221, an outer body 222, air inlets 223, and coupling depressions 224.

The inner body 221 may be formed in an approximately cylindrical shape to be coupled to the air outlet 212 of the front cover 210. In other words, the inner diameter of the inner body 221 may be the same as the inner diameter of the air outlet 212 of the front cover 210.

The outer body 222 is formed in an approximately cylindrical shape to be coupled to the outer circumference of the front cover 210. In other words, the outer diameter of the outer body 222 is the same as the outer diameter of the front cover 210.

The air inlets 223 are plural in number, and are formed between the inner body 221 and the outer body 222. These air inlets 223 function to suck air from the plurality of air suction holes 211 provided through the front cover 210 and to transfer the air to the silicon carbide honeycomb heater 230 and/or an air circulation fan (not shown).

In this case, although the air circulation fan is not shown in the drawings, the sterilization and drying device 200 according to an embodiment of the present invention may include the above-described components/materials of the sterilization and drying device 100 shown in FIGS. 1a to 1c without changes.

The coupling depressions 224 are formed between the inner body 221 and the outer body 222, and connect the inner body 221 and the outer body 222 to each other. Accordingly, the inner body 221 is maintained at a predetermined location inside the outer body 222.

Furthermore, the coupling depressions 224 have shapes depressed from the inner body 221 to the outer body 222 to a predetermined depth and a predetermined length, and thus the coupling depressions 224 are coupled to the coupling protrusions 213 of the above-described front cover 210.

The silicon carbide honeycomb heater 230 has an approximately circular plate shape in a mesh form, and may include a plurality of coupling rings 231 formed around the silicon carbide honeycomb heater 230. These coupling rings 231 are coupled to a retainer ring 225 to be described later, and thus the silicon carbide honeycomb heater 230 is coupled to the inside of the body 220.

Furthermore, the back cover 240 also has an approximately circular plate shape, and may include a plurality of coupling rings 241 formed around the back cover 240. These coupling rings 241 are also coupled to the retainer ring 225 to be described later, and thus the back cover 240 completely blocks the back of the body 220.

In this case, the front cover 210, the body 220, and the back cover 240 may be made of, for example, but not exclusively, thermoplastic resin such as polyethylene, polypropylene, polyvinyl chloride, polystyrene, ABS resin, AS resin, methacrylic resin, polyvinyl alcohol, polyvinylidene chloride, or engineering plastic, thermosetting resin such as phenol resin, urea resin, melamine resin, alkyd resin, unsaturated polyester resin, epoxy resin, polyurethane resin, silicon resin, or diallylphtalate resin, or the like which has superior thermal resistance and chemical resistance. Furthermore, the front cover 210, the body 220, and the back cover 240 may be made of ceramic, metal, or the like.

Figure 5A:
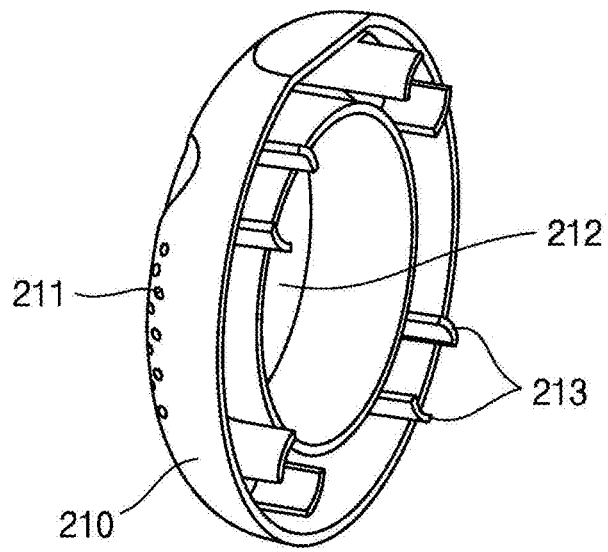
FIGS. 5a and 5b are back perspective views showing a front cover and a body in the sterilization and drying device according to the various embodiments of the present invention, respectively.
Figure 5B:
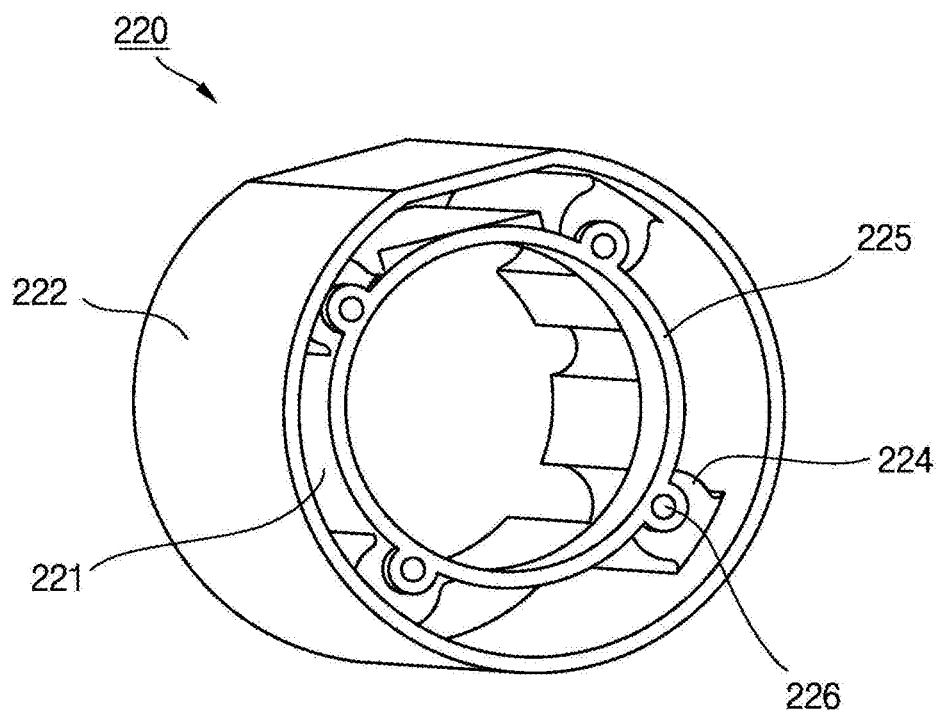

Referring to FIGS. 5a and 5b, the back perspective views of the front cover 210 and the body 220 in the sterilization and drying device 200 according to the various embodiments of the present invention are shown.

As shown in FIG. 5a, in the sterilization and drying device 200 according to the various embodiments of the present invention, the front cover 210 may further include coupling protrusions 213 which extend backward to a predetermined length, thereby enabling the coupling protrusions 213 to be coupled to the coupling depressions 224 provided on the body 220.

Furthermore, as shown in FIG. 5b, in the sterilization and drying device 200 according to the various embodiments of the present invention, the retainer ring 225 which is installed between the inner body 221 and the outer body 222 and to which the silicon carbide honeycomb heater 230 is coupled may be further included behind the body 220.

In particular, the retainer ring 225 is installed on the bottoms of the coupling depressions 224 provided on the body 220 via coupling rings 226, and thus there is no need for the provision of a separate support member for fastening the retainer ring 225.

In this case, the coupling rings 231 provided on the silicon carbide honeycomb heater 230 and the retainer ring 225 may be made of thermal insulators in order to prevent heat from being directly transferred from the honeycomb heater 230 to the body 220 and the back cover. The thermal insulators may include, for example, but not exclusively, phenol foam (PF) insulators, glass-wool insulators, or the like.

As described above, in the sterilization and drying device 200 according to the various embodiments of the present invention, ultraviolet rays and/or electromagnetic waves are not generated, and air inside a sterilization target can be sterilized, purified, dried, and heated by far-infrared rays which are generated by the silicon carbide honeycomb heater.

In other words, the conventional product using a UV lamp is disadvantageous in that ultraviolet rays themselves are harmful to a human body, a fluorescent material, etc. inside the lamp exert a harmful influence on a human body when the lamp is broken, and unicellular bacteria, such as colon bacilli, are killed and resume activities immediately after the lamp is turned off. Furthermore, the metal heater heating method is disadvantage in that heating time is long, power consumption is high and energy use efficiency is low. However, the sterilization and drying devices 100 and 200 according to the various embodiments of the present invention adopts a ceramic heater, i.e., the silicon carbide honeycomb heater, and are thus advantageous in that a high energy use efficiency of 97.1% is achieved (based on KTL authentication tests) using an instantaneous heating method. Furthermore, the lamp method and the metal heater heating method generate large quantities of electromagnetic waves simultaneously with sterilization, whereas the silicon carbide ceramic sterilization heater has an advantage in that electromagnetic waves are not generated. Furthermore, the lamp method does not exert an influence on a location which is reached by light, whereas the ceramic heater method can apply far-infrared rays to all locations and sterilize the locations by using an air convection method (i.e., an area around a sterilization target can be also sterilized).

In particular, the silicon carbide ceramic honeycomb heater can reduce power consumption by about 40% or higher, can directly kill mold fungi by using an instantaneous heating method, can kill 99.9% or higher of colon bacilli and staphylococci, can emit a large quantity of far-infrared rays (the far-infrared ray emission rate is 92%), and can eliminate fine dust and malodor by directly decomposing them.

Moreover, the silicon carbide ceramic honeycomb heater is advantageous in that it can block electromagnetic waves rather than emitting electromagnetic waves as a honeycomb-shaped module, in that it is of a module type and is thus easily disassembled, so that killed bacteria bodies can be washed away and thus it can be used in a more hygienic manner, in that additional cost is not incurred due to its semi-permanent use, and in that bacteria killing efficiency is significantly high due to the use of a heat convection method.

The sterilization and drying device according to the various embodiments of the present invention which does not generate ultraviolet rays and/or electromagnetic waves and which can sterilize, purify, dry and heat air inside a sterilization target by means of far-infrared rays.

In other words, the sterilization and drying device according to the various embodiments of the present invention sucks air inside a sterilization target via the air suction holes, air inlets, and the air circulation fan, sterilizes, purifies, dries and heat the air via the silicon carbide honeycomb heater by means of far-infrared rays, and discharges the air into the sterilization target through the air outlet, thereby rapidly heating and drying the sterilization target and also sterilizing and purifying the inside of the sterilization target.

The above-described embodiments are merely embodiments used to illustrate the practice of the sterilization and drying device according to the present invention. The present invention is not limited to the embodiments. It will be apparent to those skilled in the art that various modifications and alterations may be made without departing from the spirit of the present invention set forth in the attached claims.

What is claimed is:

1. A sterilization and drying device, comprising:
   a body configured to be coupled to an inside of a sterilization target, and to suck and discharge internal air of the sterilization target;
   a silicon carbide honeycomb heater installed inside the body, and configured to sterilize, purify, dry, and heat the sucked air and discharge the sterilized, purified, dried, and heated air;
   an air circulation fan installed behind the silicon carbide honeycomb heater, and configured such that the internal air of the sterilization target is sucked, passed through the silicon carbide honeycomb heater, and then discharged; and
   a battery installed on one side of the air circulation fan, and configured to supply power to the silicon carbide honeycomb heater and the air circulation fan,
   wherein the body has a tube shape, and includes a plurality of air inlets which are formed on an inside surface of the body in a lengthwise direction and which extend from a front of the body to a back of the air circulation fan, and
   wherein the air inlets further include a plurality of air suction holes which are formed through the body.

2. The sterilization and drying device of claim 1, wherein the internal air of the sterilization target is sucked to the air circulation fan through the air suction holes of the air inlets, and the air sterilized, purified, dried, and heated via the silicon carbide honeycomb heater is discharged through the front of the body.

3. A sterilization and drying device, comprising:
   a body configured to be coupled to an inside of a sterilization target, and to suck and discharge internal air of the sterilization target;
   a silicon carbide honeycomb heater installed inside the body, and configured to sterilize, purify, dry, and heat the sucked air and discharge the sterilized, purified, dried, and heated air;
   an air circulation fan installed behind the silicon carbide honeycomb heater, and configured such that the internal air of the sterilization target is sucked, passed through the silicon carbide honeycomb heater, and then discharged;
   a battery installed on one side of the air circulation fan, and configured to supply power to the silicon carbide honeycomb heater and the air circulation fan; and
   a front cover which is coupled to the front of the body and which includes a plurality of air suction holes configured to suck the internal air of the sterilization target and an air outlet configured to discharge the sterilized, purified, dried, and heated air,
   wherein the body includes:
   an inner body coupled to the air outlet of the front cover;
   an outer body coupled to an outer circumference of the front cover; and
   a plurality of air inlets configured to suck air from the air suction holes of the front cover between the inner body and the outer body, and to transfer the air to the air circulation fan.

4. The sterilization and drying device of claim 3, wherein:
   the front cover further includes coupling protrusions extended backward;
   the body further includes coupling depressions formed between the inner body and the outer body; and
   the coupling protrusions of the front cover are coupled to the coupling depressions of the body.

5. The sterilization and drying device of claim 3, wherein the body further includes a retainer ring installed behind the inner body and the outer body and configured such that the silicon carbide honeycomb heater is coupled thereto.

6. The sterilization and drying device of claim 5, wherein the silicon carbide honeycomb heater further includes coupling rings configured to be coupled to the retainer ring, and the retainer ring and the coupling rings are made of thermal insulators configured to prevent heat from being transferred from the honeycomb heater to the body.

7. A sterilization and drying device, comprising:
   a front cover comprising a plurality of air suction holes, and a first air outlet; wherein said plurality of air suction holes are formed to suck internal air of a sterilization target; and said first air outlet is formed to discharge sterilized and dried air;
   a body coupled to the front cover, and configured such that air inlets formed in regions corresponding to the air suction holes and a second air outlet formed in a region corresponding to the first air outlet are included;

a silicon carbide honeycomb heater coupled to a back of the body, and configured to have a size corresponding to that of the second air outlet; and a back cover coupled to the silicon carbide honeycomb heater, and configured to seal the back of the body.

8. The sterilization and drying device of claim 1, wherein the sterilization target is one of a shoe, a garment, a shoe closet, and a pet dog.

\* \* \* \* \*